(12) United States Patent
Hepp et al.

(10) Patent No.: US 11,446,199 B2
(45) Date of Patent: Sep. 20, 2022

(54) HAND ORTHOSIS, MODULE MEMBER FOR USING IN A HAND ORTHOSIS, AND METHOD FOR PRODUCING A HAND ORTHOSIS

(71) Applicant: HKK BIONICS GMBH, Ulm (DE)

(72) Inventors: Dominik Hepp, Jettingen-Scheppach (DE); Tobias Knobloch, Ulm (DE)

(73) Assignee: HKK BIONICS GMBH, Ulm (DE)

( * ) Notice: Subject to any disclaimer, the term of this patent is extended or adjusted under 35 U.S.C. 154(b) by 441 days.

(21) Appl. No.: 16/824,288

(22) Filed: Mar. 19, 2020

(65) Prior Publication Data

US 2020/0281798 A1    Sep. 10, 2020

Related U.S. Application Data (63) Continuation of application No. PCT/EP2018/075448, filed on Sep. 20, 2018.

(30) Foreign Application Priority Data

Sep. 20, 2017    (EP) .................................... 17192053

(51) Int. Cl.
*A61H 1/02*    (2006.01)
*A61F 5/01*    (2006.01)

(52) U.S. Cl.
CPC .......... *A61H 1/0288* (2013.01); *A61F 5/013* (2013.01); *A61F 2005/0155* (2013.01); *A61H 2201/0107* (2013.01); *A61H 2201/165* (2013.01); *A61H 2201/1638* (2013.01)

(58) Field of Classification Search
CPC .......... A61H 1/0288; A61H 2201/0107; A61H 2201/1638; A61H 2201/165; A61F 5/013; A61F 2005/0155; A61F 2/583; A61F 2/586; A61F 2002/30426; A61F 2002/5049;
(Continued)

(56) References Cited

U.S. PATENT DOCUMENTS

| 2,545,452 A | 3/1951 | Fletcher |
| 2,582,234 A | 1/1952 | Conzelman, Jr. et al. |
| 5,178,137 A | 1/1993 | Goor et al. |

(Continued)

FOREIGN PATENT DOCUMENTS

| WO | WO 03/017879 A1 | 3/2003 |
| WO | WO 2006/063347 A2 | 6/2006 |
| WO | WO 2016/088071 A1 | 6/2016 |

*Primary Examiner* — Garrett K Atkinson
(74) *Attorney, Agent, or Firm* — Muncy, Geissler, Olds & Lowe, P.C.

(57) ABSTRACT

A hand orthosis for bending and/or stretching at least one finger of a patient's hand, comprising a force-introducing device fastened to a splint, which is coupled with at least one finger segment paired with the finger of the patient's hand, wherein the at least one finger segment comprises a plurality of modular members interconnected in an articulated manner. The modular members each have at least one bayonet link on a first front side and at least one bayonet hook, corresponding to the bayonet link, on a second front side for the formation of a bayonet connection between adjacent modular members providing a bayonet joint. In addition, the invention relates to a modular member for using in a hand orthosis and a method of producing a hand orthosis.

15 Claims, 7 Drawing Sheets

(58) Field of Classification Search
CPC ...... A61F 2002/5053; A61F 2005/0165; A61F 2005/0146; A61F 5/0118
See application file for complete search history.

(56) References Cited

U.S. PATENT DOCUMENTS

| | | |
|---|---|---|
| 2008/0188952 A1 | 8/2008 | Veatch et al. |
| 2010/0204804 A1* | 8/2010 | Garrec ................. A61H 1/0277 623/24 |
| 2011/0313331 A1* | 12/2011 | Dehez ................. A61H 1/0285 601/33 |
| 2014/0172166 A1* | 6/2014 | Kim .................... A61H 1/0285 601/5 |
| 2017/0014141 A1* | 1/2017 | Cameron ........... A61B 17/1617 |
| 2017/0119570 A1* | 5/2017 | Beck ......................... A61F 5/10 |
| 2017/0266075 A1* | 9/2017 | Becchi .................. A63B 23/16 |
| 2019/0209086 A1* | 7/2019 | Huang ............... A41D 19/0027 |
| 2020/0038285 A1* | 2/2020 | Bauer .................... A61H 23/00 |
| 2021/0162259 A1* | 6/2021 | D'Addario ........... A63B 21/023 |
| 2022/0039983 A1* | 2/2022 | Hislop ................... A61F 5/013 |

* cited by examiner

HAND ORTHOSIS, MODULE MEMBER FOR USING IN A HAND ORTHOSIS, AND METHOD FOR PRODUCING A HAND ORTHOSIS

This nonprovisional application is a continuation of International Application No. PCT/EP2018/075448, which was filed on Sep. 20, 2018, and which claims priority to European Patent Application No. 17192053.1, which was filed on Sep. 20, 2017, and which are both herein incorporated by reference.

BACKGROUND OF THE INVENTION

Field of the Invention

The present invention relates to a hand orthosis for bending and/or stretching at least one finger of a patient's hand, comprising a force-introducing device fastened to a splint, which is coupled to at least one finger segment paired with the finger of the patient's hand, the at least one finger segment comprising a plurality of modular members that are interconnected in an articulated manner. The invention further relates to a modular member for using in a hand orthosis and to a method for producing a hand orthosis.

Description of the Background Art

Orthoses of this type are habitually used in stroke patients or other patients with limited motor ability to actively move their fingers. In this way, they are able to move their fingers despite the lack of motor skills and again able to grasp objects securely. Such hand orthoses are therefore an important tool for providing the patient with a certain self-sufficiency and for restoring some quality of life.

Hand orthoses of the type mentioned above are already known from the prior art, for example from WO 2016/088071, which corresponds to US 2017/0266075. The finger segments of the hand orthosis shown therein are made up of individual modular members which are coupled to one another by a chain. By connecting the modular members via the chain, it is possible to adjust the axial distance between individual modular members relative to each other. However, it has proven to be very disadvantageous that the chain between the modular members is very costly to produce and assemble, and that it also results in relatively tall and chunky finger segments. This poses the risk that the patient, for example when pulling on a jacket, gets the hand orthosis caught in the sleeve, so that the hand orthosis is ultimately a hindrance and the patient is forced to take the hand orthosis off more frequently.

The hand orthosis known from U.S. Pat. No. 5,178,137 has finger segments formed of outer and inner modular members, which are firmly interconnected and can be pivotably adjusted with respect to one another. The finger segments can be bent and stretched using a spindle drive. However, it has been proven to be a disadvantage that when using the finger segments known from U.S. Pat. No. 5,178,137, they can only be adjusted very slowly by the spindle drive. In addition, it is difficult to customize the finger segments to fingers of different lengths, and the mechanism of the finger segments shown therein also tends to jam.

SUMMARY OF THE INVENTION

It is therefore an object of the present invention of reducing the disadvantages mentioned above. Furthermore, it is an object of the present invention to provide an improved modular member for using in a hand orthosis and an improved method for producing a hand orthosis.

In an exemplary embodiment, a part of the object relating to the hand orthosis is achieved in that the modular members respectively comprise at least one bayonet link on a first front side and at least one bayonet hook, corresponding to the bayonet link, on a second front side, for forming a bayonet connection that provides a bayonet joint between adjacent modular members.

This makes it possible to simply interconnect the individual modular members in an articulated manner, while at the same time ensuring that the modular members connected to one another by the bayonet connection cannot separate from one another when they are installed in the hand orthosis. Namely, for releasing the bayonet connection, a relative rotation between the modular members secured by the bayonet connection is necessary, which is difficult to do in the assembled state. In this case, it has been proven to be particularly favorable when the rotational angle for the formation and release of the bayonet connection is between 40° and 90°, preferably between 50° and 70° and particularly preferably 65°. This ensures that the bayonet connection, which connects neighboring modular members, cannot accidentally become disengaged.

In order to promote the flexibility between the modular members connected by the bayonet connection, it has also proven to be advantageous if the bayonet link and the bayonet hook are each provided in plurality and are arranged at an angle to one another which is between 40° and 170°, preferably between 60° and 160° and particularly preferably 120°. By the bayonet links and hooks being arranged on an imaginary circle in a plane perpendicular to the finger axis, not opposite each other, which would correspond to an angle of 180°, but instead are disposed at an angle differing therefrom, the bayonet connection ultimately creates a bayonet joint that enables simple tilting of adjacent modular members relative to one another. Here, it has proven particularly useful if the bayonet link and the bayonet hook are provided twice. According to the present invention, however, in this case it is also provided that the bayonet link and the bayonet hook are each provided in triplicate.

It has also been found to be advantageous if the bayonet connection of adjacent modular members is configured in such a way that an axial adjustment is possible in the longitudinal direction of the finger segment of the modular members connected by the bayonet connection relative to one another. This ensures in a simple manner that the length changes occurring on the upper side of the fingers when the fingers of the patient's hand are bent can be compensated for by the modular members, since these are not only designed to be pivotable by means of the bayonet connection but are also designed to be movable in the axial direction. This is advantageously achieved by the design of the bayonet link having a hook receptacle for this purpose, in which the corresponding bayonet hook is accommodated in its final position and is axially adjusted there. The bayonet hooks are thus first introduced into the bayonet link and follow it. In this context, the two adjacent modular members are adjusted about the rotational angle and moved toward each other. When the final position is reached, the bayonet hooks are in the hook receptacles, so that the adjacent modular members can be adjusted in the axial direction relative to one another. The bayonet hooks and the bayonet link also form a movement-limiting stop and a corresponding counter-stop, which limit tilting of individual modular members relative to one another, thereby preventing the modular members from popping out.

A receptacle can be formed on the first front side of the modular members in order to receive a projection formed in each case on the second front side of adjacent modular members, in such a way that a roofing is formed between adjacent modular members. By means of the roofing, it is achieved in particular that a buckling of the coupling elements transferring the force from the force-introducing device to the finger segments is effectively prevented. Otherwise, at too high a pressure, there would be the risk of the coupling elements being plastically deformed. In addition, the roofing ensures that no gaps are created even with a bent finger, which could otherwise cause a pinching injury. Ultimately, the roofing also provides protection for the coupling elements.

It has also been found to be advantageous when the distal end of the splint is paired with a glove section, and when a palmar support is provided which engages around the glove section on its side facing the palm of the hand and which is at least partially releasably fastened to the distal end of the splint. This makes it particularly easy to put on the hand orthosis, because the patient only needs to pull the glove section onto the relevant hand and fasten the splint to the forearm. To provide the hand with additional stability in the area of the wrist, the patient only needs to place the palmar support over the palm area of the donned glove section and fasten it to the splint. This can be done, for example, by means of a snap connection. To fix the splint to the patient's forearm, a Velcro strap or an elastic band, which is secured to the splint, for example via a snap connection, has been proven particularly successful. According to the present invention, it is also provided that the palmar support is fastened to a side of the splint in an articulated manner—for example by a hinge—and on the other side is secured to the splint via the snap connection.

It has also proven advantageous for the production process if the palmar supports are made of a low-temperature thermoplastic material and if the glove section is made of silicone. Whereas a 3D scanning method can be used in the manufacture of the splint, with which the physiology of the forearm and at least part of the top of the hand can be very accurately captured and thus the splint can be customized by means of a 3D printer in a generative production process, the capturing of the geometry of the hand inner surface which would be necessary for a generative creation of the palmar support by 3D printers could be carried out only with difficulty, so that in this case, the patient-specific adjustment or manufacture must be done manually. The glove section is made of silicone based on a plaster model of the patient's hand. The use of silicone for the glove section also has the advantage of being comfortable to wear. The glove section is connected to the splint through the finger segments, can however also additionally be fastened by a screw connection.

It has also proven to be advantageous if the finger segment comprises a distal end piece and a proximal end piece, wherein the proximal end piece is fastened to the splint and the distal end piece and the modular members are fastened to the glove section. The modular members are arranged between the proximal and distal end pieces, said members also being connected via a bayonet connection to the proximal or distal end piece. For this purpose, a bayonet link is formed at the front side of the one end piece and a bayonet hook is formed at the front side of the other end piece. By attaching the proximal end piece to the splint, on the one hand, and attaching the distal end piece to the glove section, on the other, an alignment of the finger segments can also be achieved. The proximal end piece can thereby also partially be fastened to the glove section.

For anchoring the modular members in the glove section, it has also been proven if the modular members are each paired with at least one wing. In particular, when the glove section is made of silicone, the modular members can be better embedded in the silicone that is used by using the wings, wherein it has also been proven successful in this context if the wings are paired in each case with an opening and/or a barb. In particular, additional silicone material can be pressed through the opening, whereby the modular members are held better in the glove section in particular in conjunction with the barbs. However, the barbs can also be formed laterally on the modular members adjacent to the wings. Also, the wing themselves can be hook-shaped. By embedding the modular members in the material of the glove section, the translational motion of adjacent modular members is also inhibited and at the same time, said motion acts as an additional pivot point.

To prevent a bending of the outer wall, which might cause the bayonet hook to pop out of the guide and the modular members to bend further than desired, it has been found to be advantageous if the lateral areas of the modular members opposite the top side and/or the underside are reinforced.

To increase the life of the inventive hand orthosis, it has also proven advantageous if channels are formed in the splint for receiving coupling elements, which are designed to transfer tension and/or pressure forces from the force-introducing device to the finger segments. This makes it possible to accommodate the coupling elements in the splint in their entirety, so that the risk of damaging them is reduced. In addition, a particularly compact hand orthosis is obtained. According to the present invention, in terms of the coupling elements, it is particularly provided that these are formed as wires or rods and are made of a metal or a metal alloy, such as nitinol. The coupling elements can be circular and non-circular, in particular also flat, in cross section.

For assembly, it has also proven to be useful if recesses are incorporated in the splint to accommodate the force-introducing device and/or the proximal ends of the finger segments. In particular, threaded bushings can also be incorporated into the splint to which the force-introducing device and/or the proximal end pieces of the finger segments can be bolted. The recess also facilitates assembly of the force-introducing device or the finger segments and the hand orthosis can be made much flatter.

The object related to the modular member is achieved according to the invention by a modular member having at least one bayonet link formed on a first front side and at least one bayonet hook, corresponding to the bayonet link, formed on a second front side, for forming a bayonet connection between adjacent modular members. In this way, a modular member is provided that can be easily connected to adjacent modular members, while at the same time, due to the design of the bayonet connection and the bayonet link and the arrangement of the bayonet hooks, both tilting of adjacent modular members and their translational adjustment relative to each other is possible.

The part of the invention relating to the production method is achieved by a method comprising the steps: creating a glove section, customizing the length of the finger segments to the fingers of the patient's hand by selecting the number of modular members used, embedding the modular members in the upper material of the glove section, capturing the physiology of the forearm and/or the patient's hand using a 3D scanner, creating a splint based on the determined physiology, preferably using a generative production method, securing the proximal end pieces of the finger segments to the distal end of the splint, customizing the palmar support to the individual palm of the patient's hand, attaching the force-introducing device to the splint, and coupling the force-introducing device with the finger segments via the coupler.

Hereby, a method is provided, which provides a hand orthosis that is individually customized to the respective patient's hand, which is extremely comfortable to wear and at the same time offers high functionality.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
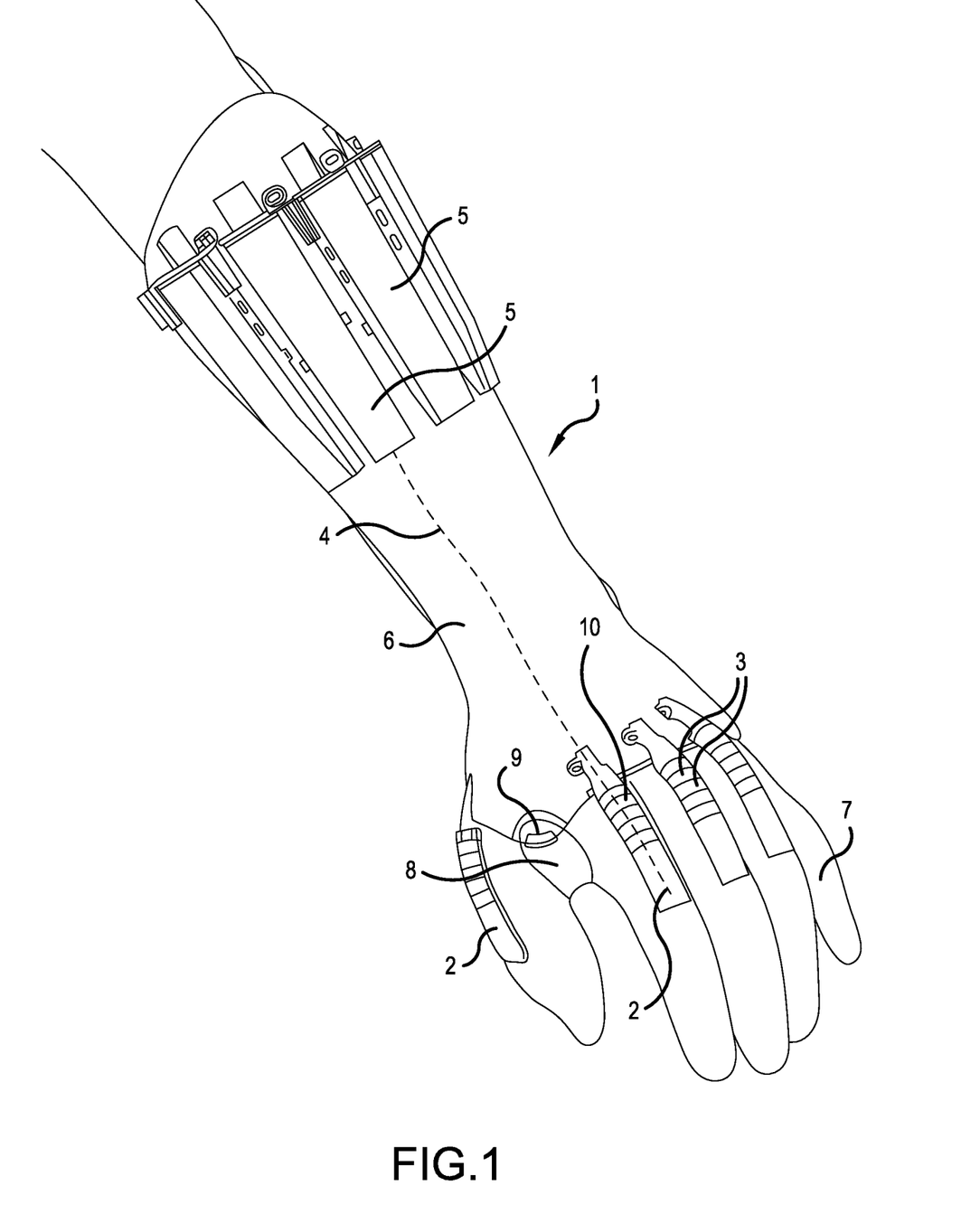
FIG. 1 is a perspective view of a hand orthosis.

FIG. 1 shows a perspective view of a hand orthosis 1 for bending and/or stretching at least one finger of a patient's hand. The hand orthosis 1 in this case comprises a plurality of finger segments 2, which each are formed of a plurality of modular members 3 interconnected in an articulated manner. The finger segments 2 are each connected at their distal ends via coupling elements 4 shaped as rods with a force-introducing device 5 formed as a servomotor, which is fastened to a splint 6 that can be fastened to the forearm of a patient. The coupling elements 4, only one of which is shown in broken lines in FIG. 1, are guided in a concealed manner in the splint 6 and the finger segments 2. The distal end of the splint 6 is paired with a glove section 7, to which the finger segments 2 are fastened. If the force-introducing device 5 now exercise a tensile or compressive force via the coupling elements 4 on the finger segment, the finger segments, and ultimately also the connected fingers, are stretched in the case of a tensile force and bent in the case of a compressive force. To support the palm of the hand, a palmar support 8 is provided which engages around the glove section 7 on its side facing the palm of the hand and which is releasably fastened to the distal end of the splint 6 by a snap connection 9. In the hand orthosis 1 illustrated in FIG. 1, the individual modular members 3 are connected to one another in an articulated manner by means of a bayonet connection 10, said connection enabling, in addition to a bending, a translational adjustment of the modular members 3 connected via the bayonet connection 10 relative to one another.

Figure 2:
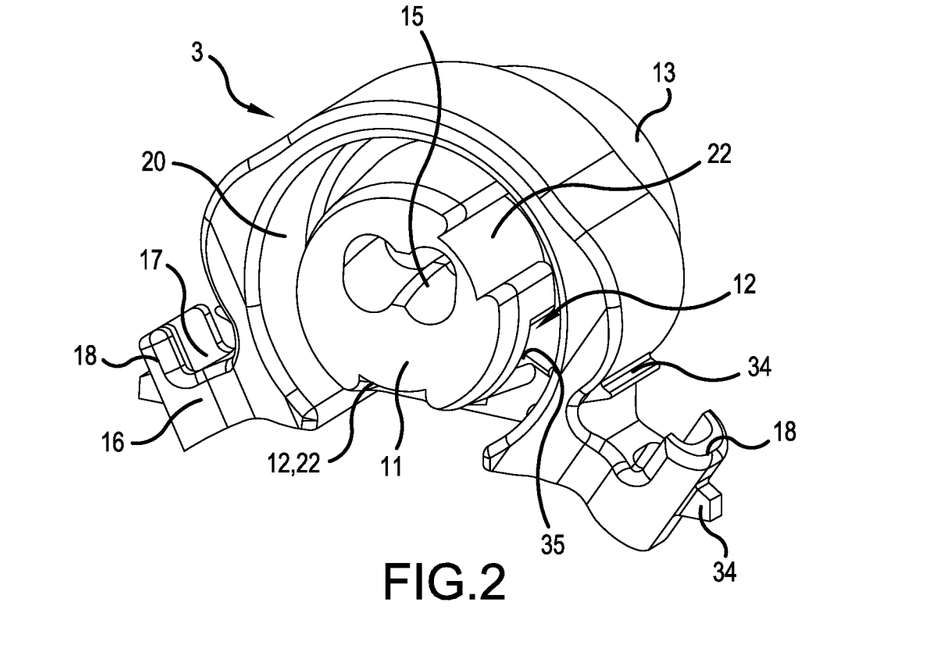
FIG. 2 is a perspective view of a first front side of a modular member of the hand orthosis.
Figure 3:
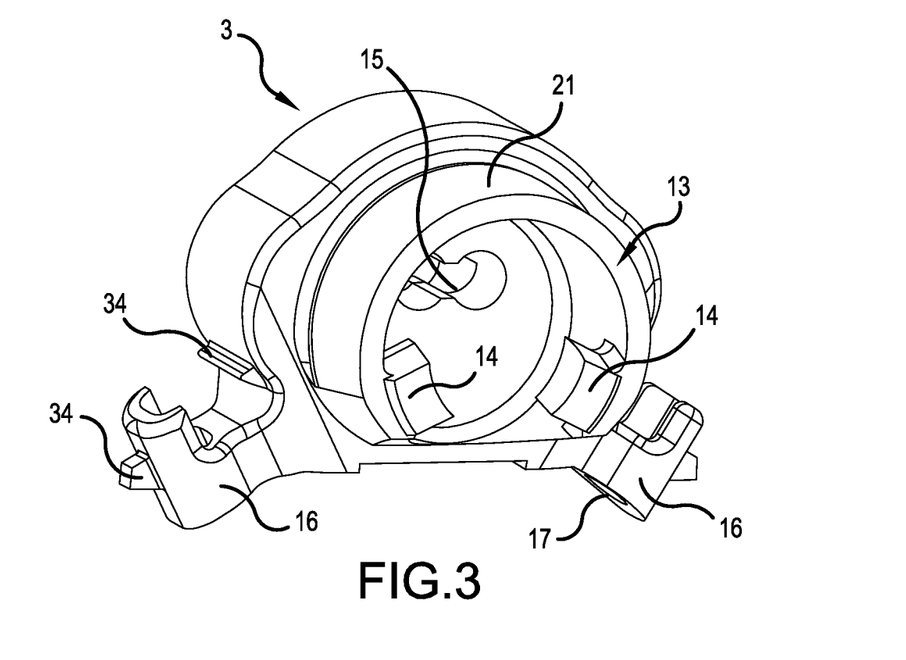
FIG. 3 is a perspective view of a second front side of the modular member.

As can be seen in FIGS. 2 and 3, bayonet links 12 are formed for the bayonet connection 10 on a first front side 11 of the modular members 3, while corresponding bayonet hooks 14 are formed on a second front side 13, which can be seen in FIG. 3.

The bayonet hooks 14 and the bayonet links 12 are not arranged opposite one another on an imaginary circle, but instead are at an angle to one another which is approximately 120° in the exemplary embodiment shown. As a result, a joint is simultaneously formed by the bayonet connection 10. The modular members have bushings 15 for the coupling elements 4, which transmit the actuating forces generated by the force-introducing device 5 to the finger segments 2 in order to bend and/or stretch these. In this case, the bushings 15 are offset upward with respect to the bayonet connection 10, in particular with respect to the bayonet hooks 14, in order to ensure better force transmission, i.e. they are disposed as far as possible from the center of rotation. As effective lever arms, the distance between the coupling elements 4 and the bayonet hooks 14 as well as the distance between the finger segments 2 and the center of rotation of the finger joint and the distance between the coupling elements 4 and the wings are superimposed. Wings 16 can also be seen laterally on the modular members 3, which serve to anchor the modular members 3 in the glove section 7. The wings 16 each have an opening 17 and are hook-shaped to form a barb 18, as a result of which the modular members 3 can be better anchored in the glove section 7. To achieve a roofing 19 in a bending or a translational motion of adjacent modular members 3 relative to one another, a receptacle 20 is formed on the first front side 11 in which a projection 21 formed on the second front side 13 of adjacent modular members 3 can engage. If the adjacent modular members 3 connected via the bayonet connection 10 are now tilted against each other, the roofing 19 will ensure that no gap forms and at the same time ensure that the bayonet connection 10 is not inadvertently released. In order to be able to strip off and remove excess silicone material when embedding the modular members 3 in the glove section 7, stripping aids 34 are provided. When embedding, excess silicone material can thus be easily stripped off, for example using a spatula placed on the stripping aids.

Figure 4:
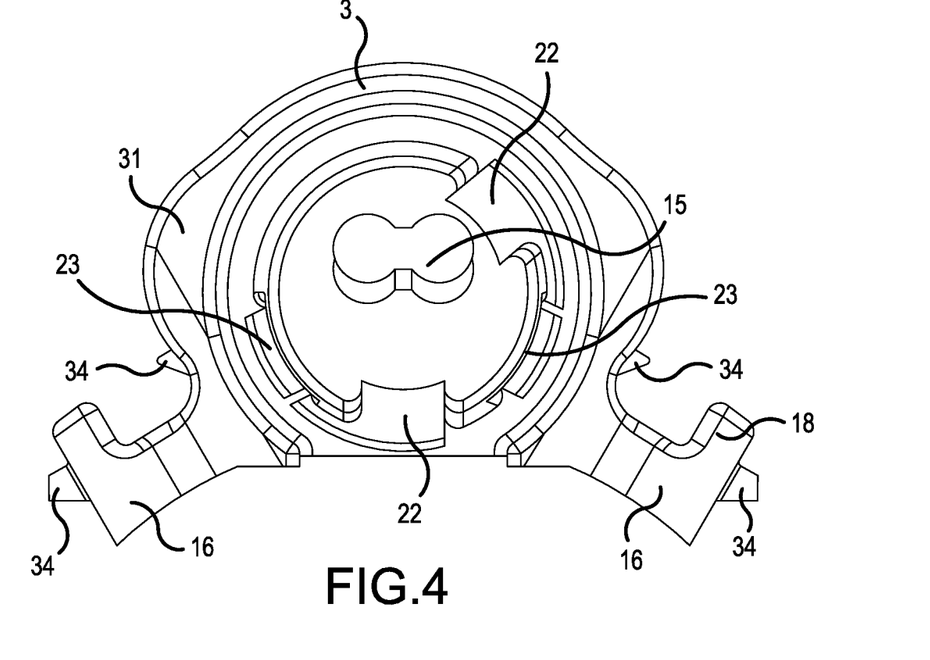
FIG. 4 is a plan view of the first front side of the modular member.
Figure 5:
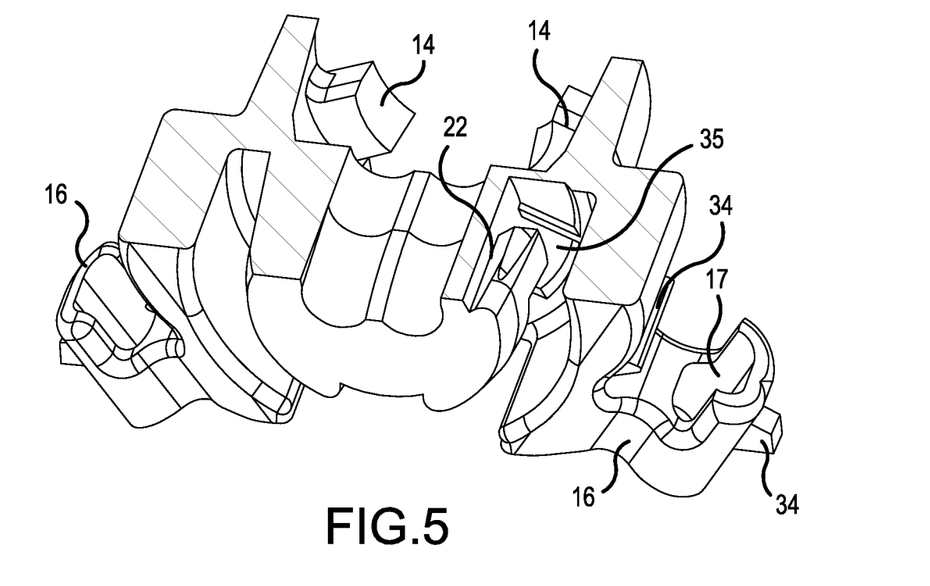
FIG. 5 is a sectional view through the modular member.

From the views of the modular member 3 shown in FIGS. 4 and 5, in particular the progression of the bayonet link 12 can be seen, which in the exemplary embodiment shown necessitates a relative rotation of adjacent modular members 3 about an angle of 65° in order to close or reopen the bayonet connection 10. In other words, the insertion openings 22 of the bayonet link 12 are rotated by an angle of approximately 65° relative to the final position 23, so that adjacent modular members 3 must also be adjusted by this angle in order to release the bayonet connection 10, thereby reducing the risk of unintentional release of the bayonet connection 10. In the final position 23, the bayonet hooks 14 are disposed in hook receptacles 35 of the bayonet links 12, in which the bayonet hooks 14 can move to a limited extent, such that an adjustment of adjacent modular members 3 in the axial direction is made possible. The hook receptacle 35 can also be seen in FIG. 2. FIG. 4 also shows that the modular member 3 has a reinforcement 31 which reinforces the modular member 3 on its side as opposed to its top.

Figure 6:
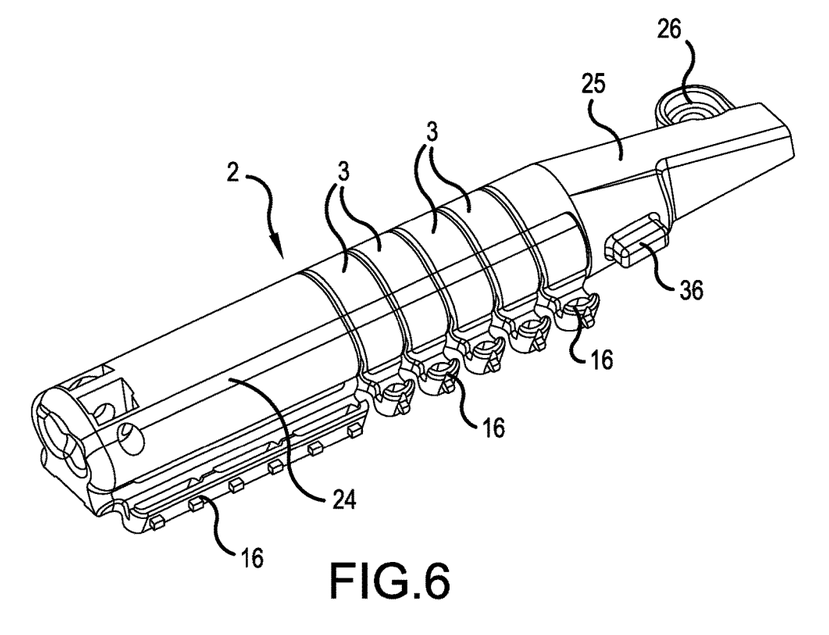
FIG. 6 is a perspective view of a finger segment.

FIG. 6 shows a perspective view of a finger segment 2 of the hand orthosis 1 according to the invention. From this it can be seen that the finger segment 2, in addition to the modular members 3, also comprises a distal end piece 24 and a proximal end piece 25, wherein the proximal end piece 25 is fastened to the splint 6 and the distal end piece 24 to the glove section 7. For this purpose, wings 16 are also formed on the distal end piece 24, with which the distal end piece 24 can be embedded in the glove section 7. The proximal end piece 25, on the other hand, additionally has—in addition to the wings 16—a screw receptacle 26 with which the finger segment 2 can be screwed onto the splint 6. In addition, the proximal end piece 25 is also paired with insertion aids 36 which can be introduced into corresponding mounting receptacle 37, which is formed in the splint 6, whereby the finger segments 2 are fastened to the splint 6.

Figure 7:
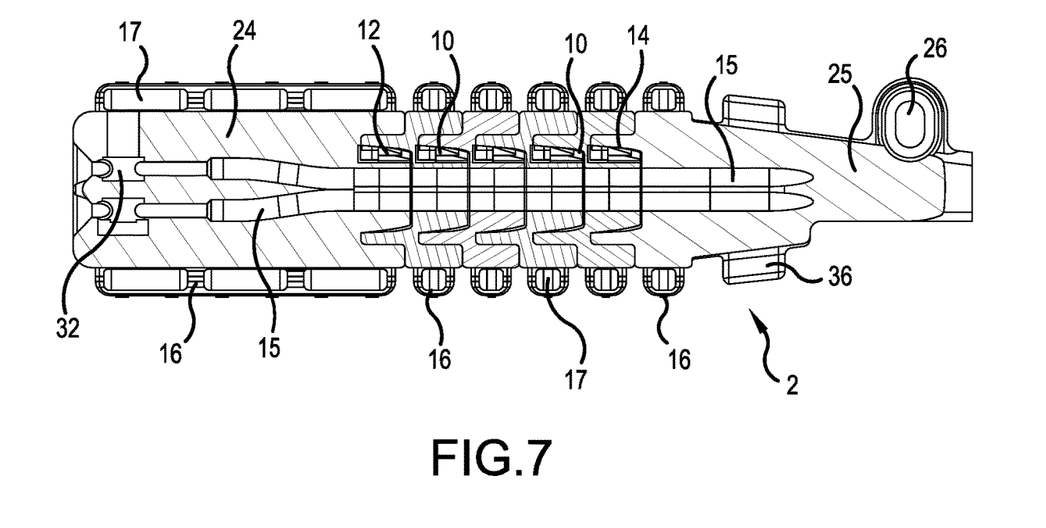
FIG. 7 is a longitudinal section through the finger segment.

As can be seen from the sectional view through the finger segment 2 shown in FIG. 7, bushings 15 are formed in the modular members 3 but also in the distal end piece 24 and in the proximal end piece 25, in which the coupling elements 4 that are connected to the force-introducing device 5 are guided to the distal end piece 24. The coupling elements 4 are then secured to the distal end piece 24 by means of a screw connection 32. It can furthermore be seen in FIG. 7 that a bayonet link 12 is formed at the proximal end of the distal end piece 24, wherein bayonet hooks 14 are provided at the distal end of the proximal end piece 25 in order to fasten the modular members 3 between the two end pieces 24, 25.

Figure 8:
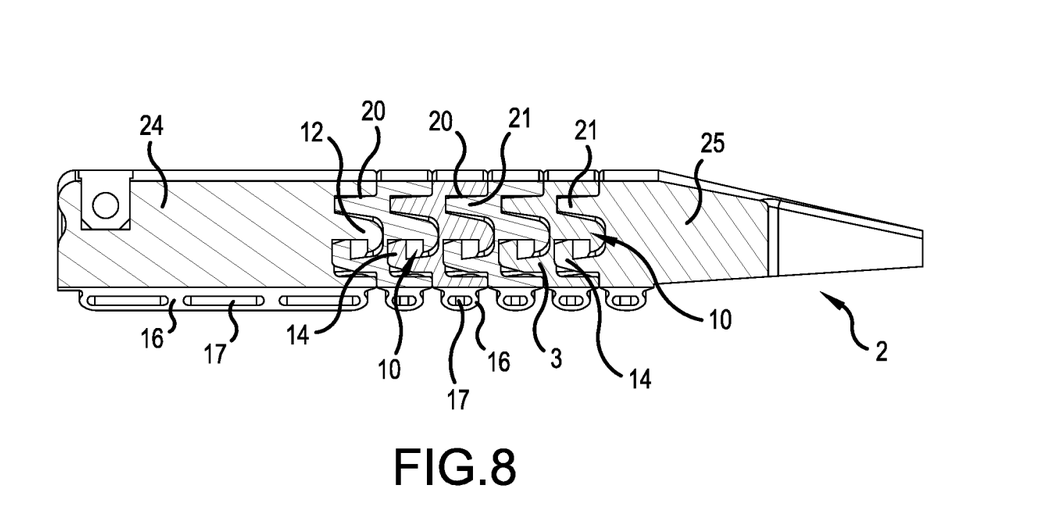
FIG. 8 is a sectional view through a stretched finger segment.
Figure 9:
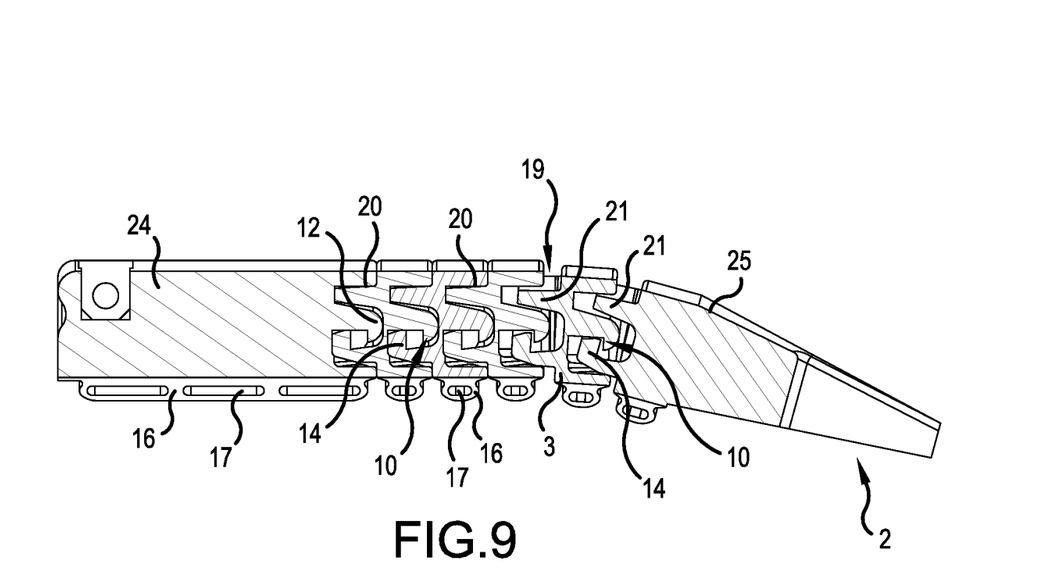
FIG. 9 is a sectional view through a bent finger segment.

The longitudinal sections through the finger segment 2 illustrated in FIGS. 8 and 9 show that by means of the bayonet connection 10, a translational displacement of adjacent modular members 3 is possible. This is particularly necessary when bending a finger in order to compensate for the change in length caused by the stretching of the skin on the top of the finger that occurs during bending. Also, the bent view of the finger segment 2 in FIG. 9 clearly shows in particular that the interaction between the receptacle 20 and the projection 21 forms the roofing 19, which prevents the coupling elements 4 from buckling under excessive pressure and from foreign bodies getting into the interior of the mechanism. When bending the finger segments 2, initially the imaginary pivot in the silicone embedding acts as a pivot. Once the bending and the translational displacement cause the bayonet hook 14 to hit the stop of the adjacent module element 3, the former acts as an additional, superimposed pivot and at the same time as stop limit both for the translatory displacement as well as for the bending. This prevents the bayonet connection 10 from opening too far, which could result in the adjacent modular members 3 popping out.

Figure 10:
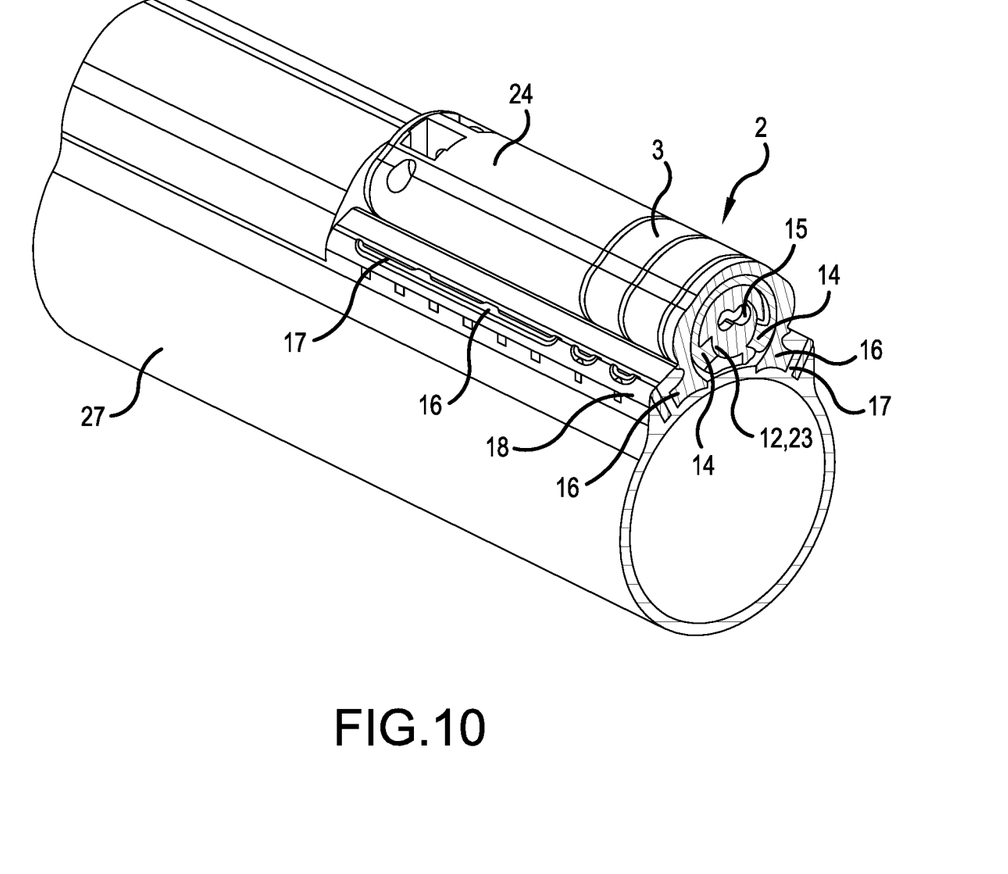
FIG. 10 is a cross section through a finger segment fastened to a glove section.

FIG. 10 shows a perspective view of a finger cot 27 of the glove section 7, to which a finger segment 2 is fastened. Both the distal end piece 24 shown in the drawing and the modular members 3 are thereby embedded in the material of the finger cot 27, which for this purpose in particular surrounds the wings 16 with the openings 17 and the barbs 18.

Figures 11, 12:
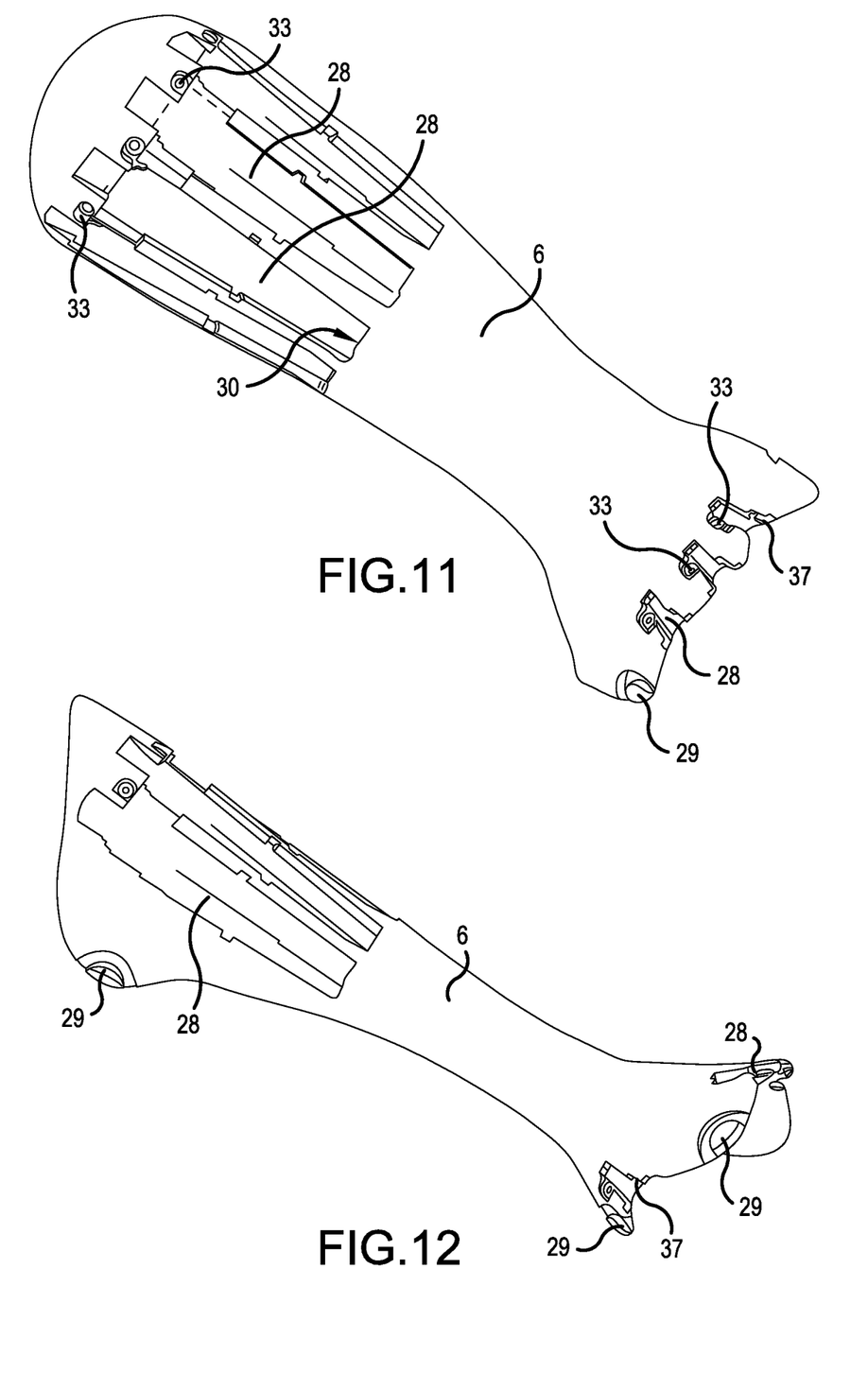
FIG. 11 is a plan view of a splint of a hand orthosis.
FIG. 12 is a side view of the splint shown in FIG. 11.

The splint 6 is shown in a plan view in FIG. 11 and in a side view in FIG. 12. From this it is particularly clear that recesses 28 are incorporated in the splint 6 for receiving the force-introducing device 5 and the proximal end pieces 25 of the finger segments 2. In order to fasten the force-introducing device 5 and the proximal end pieces 25 in the recesses, threaded bushings 33 are incorporated into the splint 6, into which the force-introducing device 5 and the proximal end pieces 25 can be screwed. Snap-in seats 29 of the snap connection 9 can also be seen, in which the palmar support 8 is fastened. In addition, it can be seen in particular from FIG. 12 that a further snap-in seat 29 is formed in the proximal region of the splint 6 in which a fastener—for example a strap—can be snapped in to fasten the splint 6 to the patient's arm. Also extending in the splint 6 are concealed channels 30 in which the coupling elements 4 that transmit the tensile and compressive forces from the force-introducing device 5 to the finger segments 2 are accommodated.

In the following, the inventive method for producing the hand orthosis 1 is again described. First, the glove section 7 is individually produced, namely based on a plaster model of the patient's hand to which silicone is applied. Here, for example, threaded bushings 33 can also be incorporated in the surface of the glove section 7, which serve to fasten the glove section 7 to the splint 6. By selecting the number of modular members 3 used, the individual finger segments 2 are customized to the length of the fingers of the patient's hand. Then, the finger segments 2—that is, the modular members 3 and the distal end pieces 24 and the proximal end pieces 25—are embedded in the upper material of the glove section 7, which is preferably made of silicone. This is advantageously done by anchoring the finger segments 2 with the wings 16 in the silicone material, that is to say they are surrounded by the silicone, wherein the silicone material penetrates the openings 17 of the wings 16. The barbs 18 provide additional stability. For this purpose, silicone strips are first applied to the underside of the wings 16 and pushed through the gaps and openings 17. The finger segments 2 are then pressed on the silicone glove and subsequently also filled with silicone from the top. Excessive silicone material, which protrudes beyond the stripping aids 34, is stripped off from the stripping aids using a spatula. Then, the physiology of the forearm and advantageously at least a part of the upper side of the patient's hand is captured by a 3D scanner, wherein the patient is already wearing the previously made glove section 7. On the basis of this data, a splint 6, which can also cover the wrist, is produced by a generative production method—preferably by a 3D printer. During production, the recesses 28 necessary for the attachment of the finger segments 2 as well as the force-introducing device 5 and the channels 30 are already incorporated. Also, at this time, the snap-in seats 29 for fixing the palmar supports 8 are integrally produced. The threaded bushings 33 are then subsequently worked into the splint 6. The proximal end pieces 25 of the finger segments 2 are fastened to the distal end of the splint 6 in the recess 28 provided for this purpose. To this end, the insertion aids 36 formed on the proximal end pieces 25 are inserted into the mounting receptacles 37 of the splint 6 and screwed onto the splint 6 with the screw receptacle 26. Then, in a final step, the palmar support 8 is customized to the patient's individual palm. To this end, it has proven to use a low-temperature thermoplastic material, because this can easily be modeled and customized to the physiology of the patient's hand. Here, the structures required for the snap connection 9 with the splint 6 are also formed.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A hand orthosis for bending and/or stretching at least one finger of a patient's hand, the hand orthosis comprising:
   a splint;
   a force-introducing device fastened to the splint that is coupled with at least one finger segment configured to be paired with the patient's finger,
   wherein the at least one finger segment has a plurality of modular members interconnected in an articulated manner,
   wherein the modular members respectively comprise at least one bayonet link on a first front side and at least one bayonet hook corresponding to the bayonet link on a second front side to form a bayonet connection between adjacent modular members that provides a bayonet joint.

2. The hand orthosis according to claim 1, wherein a plurality of bayonet links and bayonet hooks are provided several times and are arranged at an angle to one another which is between 40° and 170°, or between 60° and 160° or at 120°.

3. The hand orthosis according to claim 1, wherein the bayonet connection of adjacent modular members is designed such that an axial displacement in the longitudinal direction of the finger segment of the modular members connected by the bayonet connection is made possible relative to each other.

4. The hand orthosis according to claim 1, wherein on the first front side of the modular members a receptacle is formed for receiving a projection, respectively formed on the second front side of adjacent modular members such that a roofing is formed between adjacent modular members.

5. The hand orthosis according to claim 1, wherein the distal end of the splint is paired with a glove section, and wherein a palmar support is provided, which engages around the glove section on its side facing the palm and which is at least partially releasably fastened to the distal end of the splint.

6. The hand orthosis according to claim 5, wherein the palmar support is made of a low-temperature thermoplastic material and wherein the glove section is made of silicone.

7. The hand orthosis according to claim 5, wherein the finger segment includes a distal end piece and a proximal end piece, wherein the proximal end piece is fastened to the splint and the distal end piece and the modular members are fastened to the glove section.

8. The hand orthosis according to claim 5, wherein the modular member are each paired with at least one wing for anchoring the modular members in the glove section.

9. The hand orthosis according to claim 8, wherein the wings are each paired with an opening and/or a barb.

10. The hand orthosis according to claim 1, wherein the lateral areas of the modular members are reinforced with respect to the top side and underside.

11. The hand orthosis according to claim 1, wherein channels are formed in the splint for receiving coupling elements, which transfer tensile and/or pressure forces from the force-introducing device to the finger segments.

12. The hand orthosis according to claim 11, wherein the coupling elements are selected from a group consisting of wires and rods and are connected with the force-introducing device and the finger segment.

13. The hand orthosis according to claim 1, wherein recesses are incorporated in the splint for receiving the force-introducing device and/or the proximal end pieces of the finger segments.

14. A modular member for a hand orthosis according to claim 1, the modular member comprising:
   at least one bayonet link formed on a first front side; and
   at least one bayonet hook corresponding to the bayonet link formed on a second front side for the formation of a bayonet connection between adjacent modular members.

15. A method for producing a hand orthosis according to claim 1, the method comprising:
   creating a glove section;
   customizing a length of finger segments to fingers of a patient's hand by selecting a number of modular members used;
   embedding the modular members in the upper material of the glove section;
   capturing a physiology of a forearm and/or a patient's hand using a 3D scanner;
   creating a splint based on the determined physiology via a generative production method;
   securing proximal end pieces of the finger segments to a distal end of the splint;
   customizing a palmar support to the patient's individual palm;
   fastening a force-introducing device to the splint; and
   coupling the force-introducing device with the finger segments via a coupler.

* * * * *